(12) United States Patent
Lawler

(10) Patent No.: US 9,392,853 B2
(45) Date of Patent: Jul. 19, 2016

(54) SMART PHONE CARRYING CASE

(71) Applicant: Thomas Lawler, Saginaw, MI (US)

(72) Inventor: Thomas Lawler, Saginaw, MI (US)

(*) Notice: Subject to any disclaimer, the term of this patent is extended or adjusted under 35 U.S.C. 154(b) by 312 days.

(21) Appl. No.: 14/214,725

(22) Filed: Mar. 15, 2014

(65) Prior Publication Data

US 2014/0261541 A1   Sep. 18, 2014

Related U.S. Application Data

(60) Provisional application No. 61/788,966, filed on Mar. 15, 2013.

(51) Int. Cl.
| | |
|---|---|
| *A45C 11/00* | (2006.01) |
| *A45C 15/00* | (2006.01) |
| *G02B 27/00* | (2006.01) |
| *H04B 1/3888* | (2015.01) |
| *A61L 2/22* | (2006.01) |
| *A01N 25/34* | (2006.01) |
| *B08B 1/00* | (2006.01) |
| *A47L 25/00* | (2006.01) |
| *A47L 1/15* | (2006.01) |

(52) U.S. Cl.
CPC ............ *A45C 11/00* (2013.01); *A01N 25/34* (2013.01); *A61L 2/22* (2013.01); *G02B 27/0006* (2013.01); *H04B 1/3888* (2013.01); *A45C 15/00* (2013.01); *A45C 2011/002* (2013.01); *A47L 1/15* (2013.01); *A47L 25/00* (2013.01); *B08B 1/006* (2013.01)

(58) Field of Classification Search
CPC ...... B08B 1/006; H04B 1/3888; A45C 15/00; A45C 2011/002; A45C 11/00; A01N 25/34; A01N 33/12; G02B 27/0006; A47L 1/15; A47L 25/00
USPC .................................. 15/210.1, 214; 206/38
See application file for complete search history.

(56) References Cited

U.S. PATENT DOCUMENTS

2014/0353201 A1* 12/2014 Molineux .............. B65D 33/00
                                                              206/524.3

* cited by examiner

*Primary Examiner* — Saeed T Chaudhry
(74) *Attorney, Agent, or Firm* — Reising Ethington PC

(57) ABSTRACT

A smart phone carrying case that is capable of cleaning and disinfecting a smart phone touch screen every time the phone is removed from the case is disclosed. The smart phone carrying case includes a pocket, inside of which is a cleaning and disinfecting pad, and further includes a flap that supports a drying pad. The touch screen can be cleaned by wiping it across the cleaning and disinfecting pad when the smart phone is removed from the pocket of the carrying case. The touch screen may then be wiped across the drying pad on the flap before the smart phone is operated by the user.

8 Claims, 3 Drawing Sheets

SMART PHONE CARRYING CASE

This application claims priority to and benefit of U.S. Provisional Patent Application Ser. No. 61/788,966 filed Mar. 15, 2013, the entire specification of which is expressly incorporated herein by reference.

TECHNICAL FIELD

The technical field of this disclosure relates generally to a case for carrying a smart phone.

BACKGROUND

Smart phones are some of the most prevalent mobile devices in the market today. These phones typically include a touch screen that is responsive to a user's touch. The user, for example, can touch, drag, or otherwise interact with the touch screen via fingertip contact while using the phone—e.g., while texting, calling, surfing the internet, and/or page scrolling. Functional operation of the smart phone by way of a touch screen is innovative and convenient. But the constant and repeated contact by a user's fingers can transfer dirt, oils, germs, and other unwanted substances to the touch screen. The ability to remove these substances without much hassle would be a welcome benefit to all types of smart phone users.

SUMMARY

A smart phone carrying case that is capable of cleaning and disinfecting a smart phone touch screen every time the phone is removed from the case is disclosed. The smart phone carrying case includes a pocket and a flap. To provide for efficient cleaning of the smart phone, and more specifically the touch screen of the smart phone, a cleaning and disinfecting pad is supported within the pocket and a drying pad is supported on the flap. The cleaning and disinfecting pad contains an absorbed cleaning and disinfecting solution. Each time the user removes the smart phone from the carrying case, the touch screen can be wiped, first, across the cleaning and disinfecting pad to clean and disinfect the touch screen, and second, across the drying pad to remove any residual cleaning and disinfection solution from the touch screen.

DETAILED DESCRIPTION

Figure 1:
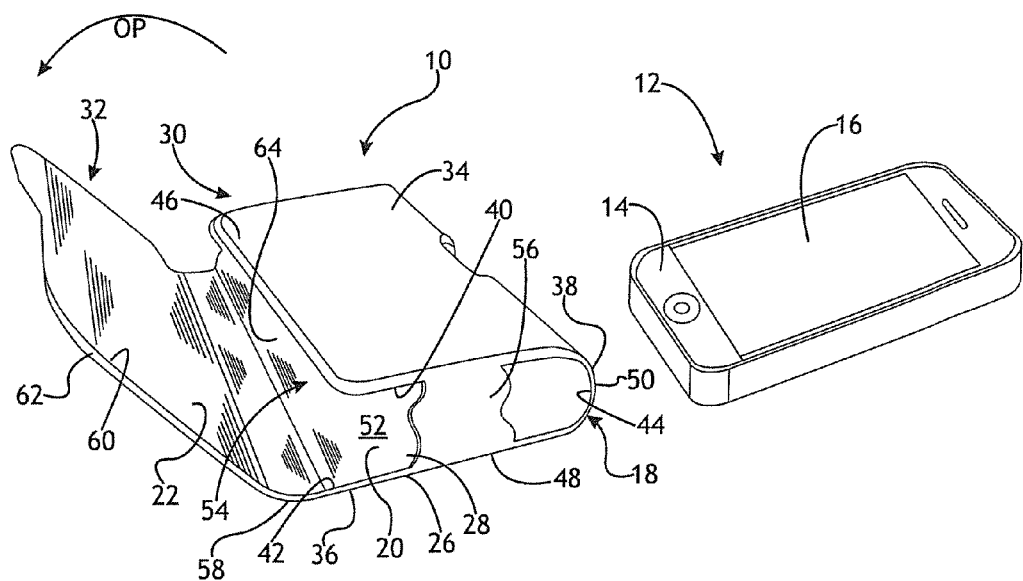
FIG. 1 is a perspective view of a smart phone and a carrying case that can carry the smart phone.
Figure 2:
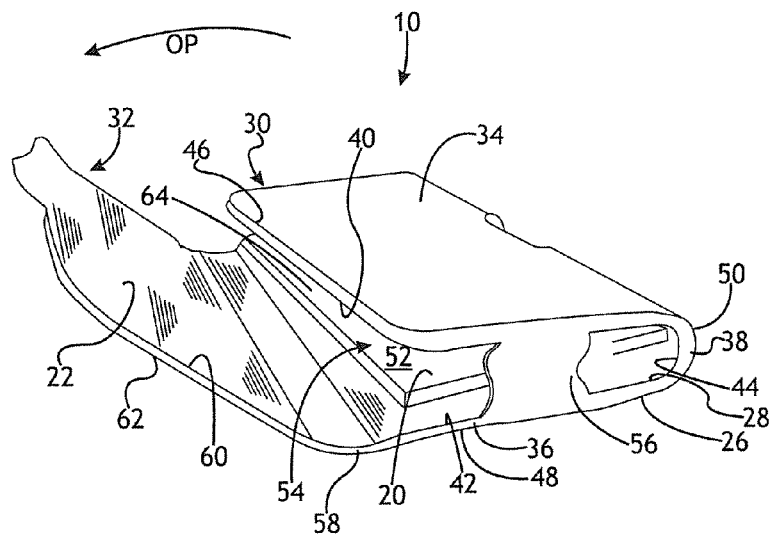
FIG. 2 is a perspective view of the carrying case in which the flap is in the open position.

FIG. 1 illustrates a preferred embodiment of a carrying case 10 for a smart phone 12. The carrying case 10 is configured to receive and hold the smart phone 12 in a protective way, and is attachable to a wide variety of articles—such as a belt, a pair of pants, a pants pocket, a briefcase pocket, etc.— to permit easy and handless transport. The smart phone 12 may be any device that includes a face 14 in which at least 50%, and preferably at least 75%, of the surface area of that face 14 is an exposed touch screen 16. Apart from holding and transporting the smart phone 12, the smart phone carrying case 10 is also configured to disinfect and dry the touch screen 16 of the smart phone 12 every time the smart phone 12 is removed from the carrying case 10.

The carrying case 10 includes a flexible member 18, a cleaner and disinfectant pad 20, a drying pad 22, and a clip 24. The flexible member 18 preferably comprises an outer layer 26 of artificial leather, such as Koskin or polyurethane, and an inner layer 28, such as a fibrous mat made from polyester fibers. The outer layer 26 and the inner layer 28 may be coextensive in size and shape, or not, and they may be sewn or otherwise bonded together. Other suitable materials may of course be used to make the flexible member 18. For example, in an alternative embodiment, leather may be used as the outer layer 26, or it may be used as the entire flexible member 18. Other materials not specifically mentioned here but known to skilled artisans may also be used to make the flexible member 18.

The flexible member 18 is arranged to provide a pocket 30 and a flap 32. The pocket 30 can receive and hold the smart phone 12. And it includes a front cover 34, a back cover 36, and a bottom fold 38 where the flexible member 18 is folded back on itself so that the front and back covers 34, 36 are connected and spaced apart from one another. Each of the front cover 34, the back cover 36, and the bottom fold 38 has an inside surface 40, 42, 44 and an outside surface 46, 48, 50. The inside surfaces 40, 42, 44 are provided by the inner layer 28 of the flexible member 18 and define a phone compartment 52 that is accessible by an opening 54 located opposite the bottom fold 38. The outside surfaces 46, 48, 50 are provided by the outer layer 26 of the flexible member 18 and protect the phone compartment 52 against impact and unwanted exposure to elements that might harm the smart phone 12. Furthermore, as shown, one or more expandable straps 56 may be associated with each of the front and back covers 34, 36 to maintain the desired spaced relation between the two covers 34, 36 and, by extension, the dimensions of the phone compartment 52.

Figure 3:
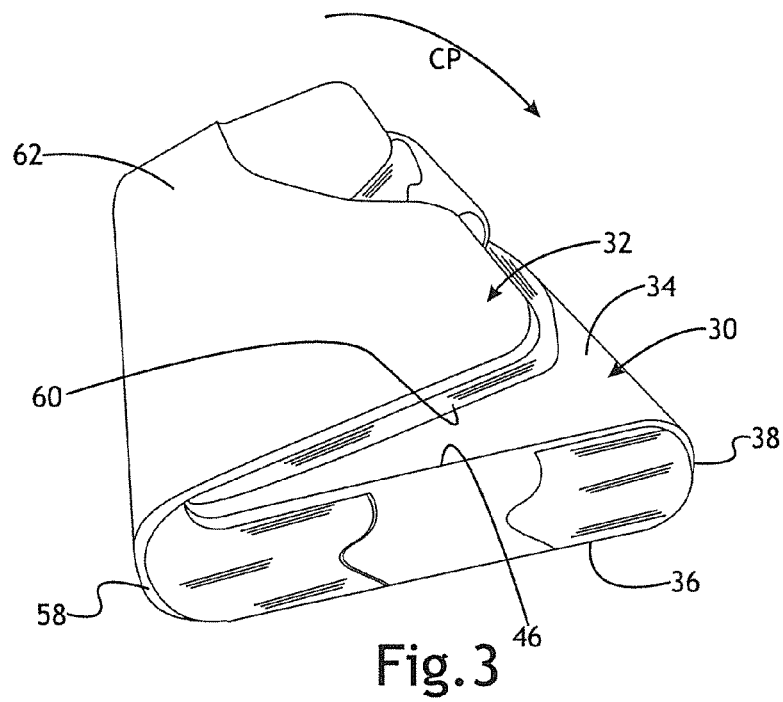
FIG. 3 is a perspective view of the carrying case in which the flap is in the closed position.
Figure 4:
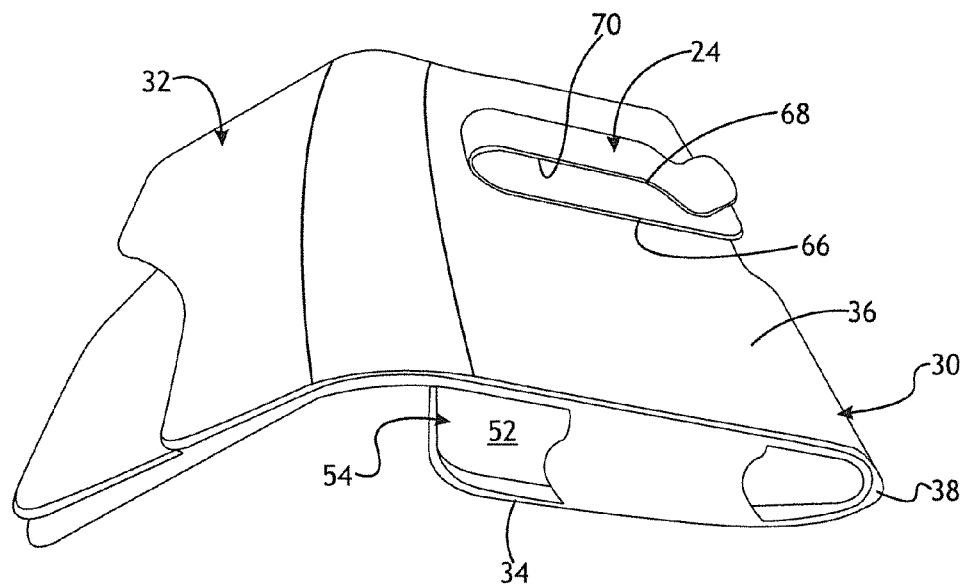
FIG. 4 is a rear perspective view of the carrying case in which the flap is in the open position.
Figure 5:
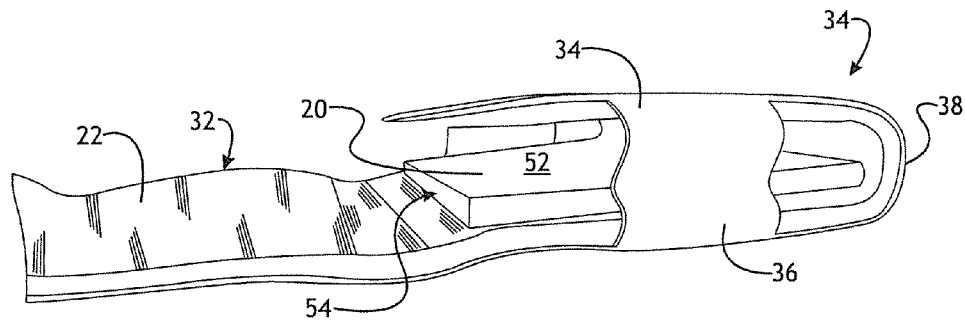
FIG. 5 is side view of the carrying case in which the flap is in the open position.
Figure 6:
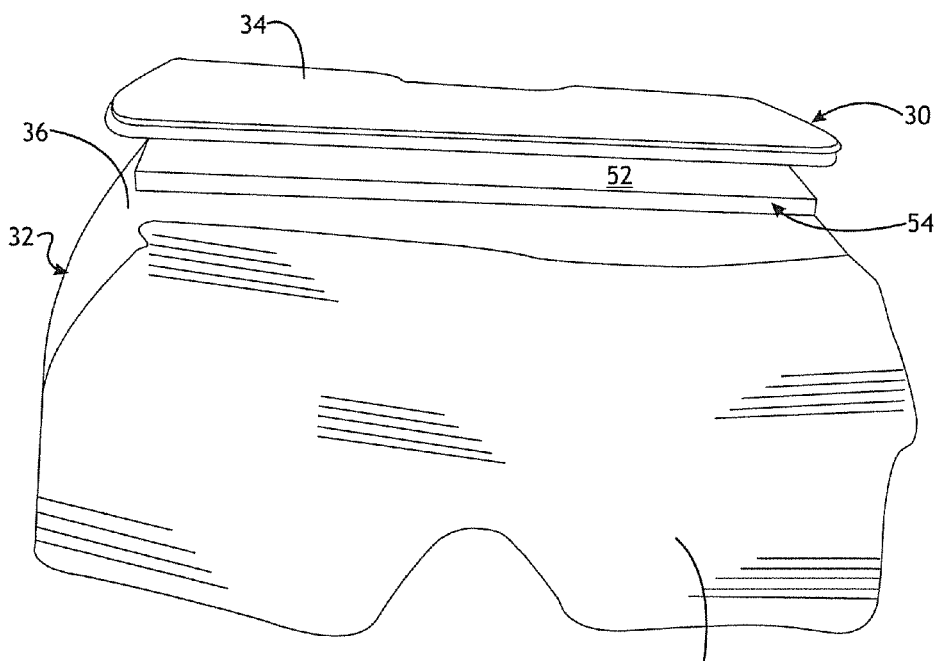
FIG. 6 is view of the carrying case from the perspective of one looking into the phone compartment of the pocket.

The flap 32 extends from the back cover 36 by way of a top fold 58 that transitions between, and joins, the flap 32 and the back cover 36. The flap 32 includes an inside surface 60, provided by the inner layer 28 of the flexible member 18, and an outside surface 62, provided by the outer layer 26 of the flexible membrane 18. Movement of the flap 32 from an open position OP (FIGS. 1-2 and 4-6) to a closed position CP (FIG. 3) is permitted by bending at the top fold 58. As shown, when the flap 32 is in the open position OP, the opening 54 to the phone compartment 52 is uncovered and the smart phone 12 can be inserted into, or removed from, the compartment 52. When the flap 32 is in the closed position CP, the flap 32 covers the opening 54 of the phone compartment 52 such that the top fold 58 is located opposite the bottom fold 38. A strap, magnet, buckle (none shown) or some other fastening mechanism may be used to hold the inside surface 60 of the flap 32 adjacent to the outside surface 46 of the front cover 34 when the flap 32 is meant to be in the closed position CP.

The cleaning and disinfecting pad 20 (hereafter "cleaning pad" for brevity) is supported on the inside surface 42 of the back cover 36. The cleaning pad 20 comprises an absorbent, non-abrasive fabric 64 and a disinfectant and cleaning solution absorbed therein. The absorbent, non-abrasive fabric 64 can be any fabric material that will not scratch the touch screen 16 of the smart phone 12 and will hold a volume of the disinfectant and cleaning solution. Several examples of acceptable fabric materials are a polyvinyl alcohol (PVA) sponge, a polyester sponge, or a meltblown polypropylene mat. The disinfectant and cleaning solution absorbed into the fabric 64 may be, for example, a solution of 0.1-1 wt. % alkyl dimethyl benzyl ammonium chlorides and 1-5 wt. % ethanol, propanol, and/or isopropanol. Cleaning and disinfecting solutions of this kind are commonly found in Lysol® and Clorox® disinfectant wipes. It will be appreciated, however, that any suitable solution that cleans and disinfects may be used.

The cleaning pad 20 may be supported on the inside surface 42 of the back cover 36 in any of a variety of ways, including sewing or velcroing the pad 20 to the flexible member 18 or bonding the pad 20 to an intermediate plate (not shown) that is held against the inside surface 42 by an adhesive, brackets, or some other suitable fastening mechanism. In a preferred embodiment, the cleaning pad 20 is removably supported on the inside surface 42 so that, when necessary, it can be replaced or replenished with additional cleaning and disinfecting solution.

The drying pad 22 is supported on the inside surface 60 of the flap 32. The drying pad 22 may be any non-abrasive fabric material such as, for example, the same fabric material used to make the cleaning pad 20 (minus the cleaning and disinfecting solution), a microfiber polyester mat, or a microfiber mat of a polyester/nylon blend. Like the cleaning pad 20, the drying pad 22 may be supported on the inside surface 60 of the flap 32 by any of a wide variety of ways, including sewing or velcroing the pad 22 to the flexible member 18 or bonding the pad 22 to an intermediate plate (not shown) that is held against the inside surface 60 by an adhesive, brackets, or some other suitable fastening mechanism. Preferably, though, the drying pad 22 is removably supported on the inside surface 60 of the flap 32 to facilitate removal, cleaning, and replacement if necessary.

The clip 24 is supported on the outside surface 48 of the back cover 36 to permit the carrying case 10 to be secured to the user's garments—such as a belt or pocket—or to some other article. The clip 24 includes a first leg 66 that is affixed, preferably rotatably, to the back cover 36, and a second leg 68 that is folded back into adjacent proximity with the first leg 66 so as to define a gap 70 in between. The second leg 68 may be biased towards the first leg 66 to make sure the legs 66, 68 can firmly hold onto whatever article is present in the gap 70 unless acted on by the user. It should be noted that the clip 24 may take on a variety of constructions besides the one specifically shown in the Figures. Any such other clip constructions may of course be used here so long as they function to secure the carrying case 24 to an intended article.

To use the smart phone carrying case 10, a user opens the case 10 by pulling back the flap 32 into its open position OP. The user then inserts the smart phone 12 into the phone compartment 52 through the opening 54 so that the touch screen 16 faces and, preferably, slides across the cleaning pad 20. The flap 32 is then pulled to its closed position CP to cover the opening 54 and confine the smart phone 12 within the phone compartment 52 for handless protected transport. Next, when the user desires to operate the smart phone 12 or remove it from the carrying case 10 for some other reason, the flap 32 is pulled to its open position OP and the smart phone 12 is removed from the phone compartment 52. During removal, the touch screen 16 is preferably wiped across the cleaning pad 20 and, subsequently, the drying pad 22. The sequence of wiping the touch screen 16 across the cleaning pad 20 and the drying pad 22 functions, first, to clean and disinfect the touch screen 16 (by wiping across the cleaning pad 20), and second, to remove any residual disinfectant and cleaning solution from the touch screen 16 (by wiping across the drying pad 22) so that the user can interface with a substantially dry touch screen 16.

The above description of preferred exemplary embodiments and are merely descriptive in nature; they are not intended to limit the scope of the claims that follow. Each of the terms used in the appended claims should be given its ordinary and customary meaning unless specifically and unambiguously stated otherwise in the specification.

The invention claimed is:

1. A carrying case for a smart phone, the carrying case comprising:
    a pocket that includes a front cover and a back cover that define, at least in part, a phone compartment accessible by an opening, the back cover supporting a cleaning and disinfecting pad inside the phone compartment, the cleaning and disinfecting pad comprising an absorbent fabric and a cleaning and disinfecting solution absorbed therein; and
    a flap that extends from the back cover and is moveable between an open position, in which the flap does not cover the opening to the phone compartment, and a closed position, in which the flap covers the opening to the phone compartment, the flap supporting a drying pad so that the drying pad faces the front cover of the pocket when the flap is in the closed position.

2. The carrying case set forth in claim 1, wherein the pocket further includes a bottom fold that connects the front and back covers, and wherein the flap extends from the back cover by way of a top fold.

3. The carrying case set forth in claim 1, wherein the cleaning and disinfecting solution comprises a solution of 0.1-1 wt. % alkyl dimethyl benzyl ammonium chlorides and 1-5 wt. % of at least one of ethanol, propanol, or isopropanol.

4. The carrying case set forth in claim 1 further comprising a clip supported by the back cover of the pocket.

5. A method of cleaning and disinfecting a touch screen of a smart phone, the method comprising:
    providing a smart phone carrying case that comprises a pocket and a flap, the pocket defining a phone compartment accessible by an opening and the flap being moveable between an open position, in which the flap does not cover the opening to the phone compartment, and a closed position, in which the flap covers the opening to the phone compartment, and wherein a cleaning and disinfecting pad is supported by the pocket inside the phone compartment and a drying pad is supported by the flap;
    removing a smart phone that comprises a touch screen from the phone compartment of the pocket so that the touch screen wipes across the cleaning and disinfecting pad; and
    wiping the touch screen across the drying pad supported on the flap after the touch screen has been wiped across the cleaning and disinfecting pad.

6. The method set forth in claim 5, wherein the cleaning and disinfecting pad comprises an absorbent fabric and a cleaning and disinfecting solution absorbed into the absorbent fabric, the cleaning and disinfecting solution comprising a solution of 0.1-1 wt. % alkyl dimethyl benzyl ammonium chlorides and 1-5 wt. % of at least one of ethanol, propanol, or isopropanol.

7. The method set forth in claim 5, wherein the drying pad comprises a polyvinyl alcohol sponge, a polyester sponge, a meltblown polypropylene mat, a microfiber polyester mat, or a microfiber mat of a polyester/nylon blend.

8. The method set forth in claim 5, further comprising:
    inserting the smart phone into the phone compartment of the pocket so that the touch screen of the smart phone faces the cleaning and disinfecting pad.

* * * * *